(12) United States Patent
Sullivan

(10) Patent No.: US 6,896,693 B2
(45) Date of Patent: May 24, 2005

(54) PHOTO-THERAPY DEVICE

(76) Inventor: Jana Sullivan, 2939 Hewlett Gulch Rd., Livermore, CO (US) 80536

( * ) Notice: Subject to any disclaimer, the term of this patent is extended or adjusted under 35 U.S.C. 154(b) by 31 days.

(21) Appl. No.: 10/152,020

(22) Filed: May 22, 2002

(65) Prior Publication Data

US 2002/0198575 A1 Dec. 26, 2002

Related U.S. Application Data

(62) Division of application No. 09/664,074, filed on Sep. 18, 2000.

(51) Int. Cl.$^7$ .............................................. A61N 5/006
(52) U.S. Cl. ............................ 607/91; 607/88; 607/90; 607/96; 606/3; 606/10
(58) Field of Search ............................... 607/80–82, 86, 607/88–96, 100, 101; 606/2, 3, 9–13; 128/898

(56) References Cited

U.S. PATENT DOCUMENTS

| | | | |
|---|---|---|---|
| 4,646,743 A | | 3/1987 | Parris |
| 4,930,504 A | * | 6/1990 | Diamantopoulos et al. . 128/395 |
| 5,086,378 A | | 2/1992 | Prince |
| 5,160,200 A | | 11/1992 | Cheselske |
| 5,187,377 A | | 2/1993 | Katoh |
| 5,278,432 A | | 1/1994 | Ignatius |
| 5,304,207 A | | 4/1994 | Stromer |
| 5,358,503 A | | 10/1994 | Bertwell |
| 5,445,608 A | | 8/1995 | Chen |
| 5,500,009 A | | 3/1996 | Mendes |
| 5,634,711 A | | 6/1997 | Kennedy |
| 5,660,461 A | | 8/1997 | Ignatius |
| 5,725,565 A | * | 3/1998 | Smith .......................... 607/88 |
| 5,766,233 A | | 6/1998 | Thiberg |
| 5,800,479 A | | 9/1998 | Thiberg |
| 5,913,883 A | | 6/1999 | Alexander |
| 5,913,884 A | | 6/1999 | Trauner |
| 6,045,575 A | * | 4/2000 | Rosen et al. .................. 607/88 |
| 6,290,713 B1 | * | 9/2001 | Russell ........................ 607/88 |
| 6,402,681 B1 | * | 6/2002 | McDonough et al. ......... 600/22 |
| 6,443,978 B1 | * | 9/2002 | Zharov ........................ 607/91 |
| 6,464,715 B1 | * | 10/2002 | Gysens et al. ................ 607/91 |
| 6,471,716 B1 | * | 10/2002 | Pecukonis .................... 607/89 |

FOREIGN PATENT DOCUMENTS

| | | |
|---|---|---|
| SU | 1266-540 | 10/1986 |
| WO | WO 94/15666 | 7/1994 |

* cited by examiner

Primary Examiner—A. Farah
(74) Attorney, Agent, or Firm—Palmer C. DeMeo

(57) ABSTRACT

A device is disclosed which is therapeutically beneficial to the well-being of living organisms such as humans, animals, and/or plant life, using photon or light waves. The device is intended to lie against the skin or surface, near the skin/surface, and/or from a distance ranging up to several feet from the skin/surface. The device is intended to be used for: general relaxation and detoxification of an organism; stimulating the healing process in an organism which is ill, diseased or injured; aiding in the elimination of pain and inflammation in an organism; stimulating/sedating the acupressure meridian system of an organism and rebalancing the electromagnetic energy-field surrounding the organism.

10 Claims, 9 Drawing Sheets

PHOTO-THERAPY DEVICE

This application is a divisional application of patent application Ser. No. 09/664,074, entitled Device and Method for Therapeutic Treatment of Living Organisms, filed on Sep. 18, 2000.

BACKGROUND OF THE INVENTION

1. Field of the Invention

This invention relates to devices containing arrays of light-emitting diodes (hereinafter LED's) which are employed in photo-therapy for various living organisms.

2. Description of the Relevant Art

Many U.S. and foreign patents disclose the use of light sources such as laser diodes and light emitting diodes emitting electromagnetic radiation of various wavelengths (i.e., colors) for administering positive and beneficial treatments to living organisms (including mammals) for injury, pain relief and illness.

U.S. Pat. No. 5,187,377 discloses LED arrays comprising a substrate and two sets of LED's emitting different colors of light which can be used as light sources for facsimile or scanner devices. The first and second sets of LED's are connected in series so that a current alternatively flows through one set or the other, in opposite directions. The two sets of LED's connected in series are further connected with each other in parallel.

U.S. Pat. No. 5,500,009 to Amron, Ltd. discusses the use of lasers and LED's in photo-therapy for the treatment of various ailments in humans. A method of treating herpes is disclosed which uses at least one LED emitting red light, preferably an array of LED's which can be directed to concentrate the light. The voltage can be varied to vary the intensity of the light, and the lights can be pulsed.

U.S. Pat. No. 5,358,503 discloses a photo-thermal therapeutic device using arrays of LED's for the simultaneous or selective treatment of areas of skin and adjacent subcutaneous structure in human subjects, utilizing photo energy and therapeutic heat. The LED array is held in a flexible or preformed holder to provide contact with the skin. Heat as well as light are provided through the LED's, and the intensity of the light and heat can be varied. Resistors cause each LED to act as a heat sink during photo-therapy treatments. This patent cites U.S. Pat. Nos. 4,535,784 and 5,024,236 which disclose photo-therapy applied to human accupuncture points.

U.S. Pat. No. 5,913,884 to Boston General Hospital discusses a method for modulating wound healing in a mammal, which employs arrays of LED or laser irradiation applied after the administration of the appropriate photo-sensitizer, which activates the light process.

U.S. Pat. No. 5,634,711 discloses hand-held portable light emitting devices suitable for photo-curing and photo-therapy applications. LED arrays are used, with means for varying the level of light energy.

U.S. Pat. No. 4,930,504 discloses devices and methods for bio-stimulation of tissue, comprising arrays of monochromatic radiation sources of multiple wavelengths. The radiation sources are arranged within the arrays so that radiation of at least two different wavelengths passes directly or indirectly through a single point within the treated tissue. Laser diodes or super-luminous diodes can be used as radiation sources. Controls are provided to turn the device on or off, vary pulse frequency and duration and time the duration of treatment. Columns 7 and 8 of the patent discuss "two-photon events" which are described as being produced by mixing of radiation of multiple wavelengths.

U.S. Pat. No. 5,766,233 to Biolight Patent Holding AB discloses devices for healing wounds and sores by photo-therapy. Arrays of LED's are held close to or in contact with the affected areas. LED's emitting infrared and red light are included, and can be pulsed in predetermined sequences for therapeutic purposes.

U.S. Pat. No. 5,278,432 to Quantum Devices, Inc. discloses apparatus for providing radiant energy, including LED arrays with power-regulating circuits, to enhance and test plant growth. Several sets of series-connected LED's are arranged on a substrate and the light intensity can be varied by the power-regulating circuit.

U.S. Pat. No. 5,913,883 discloses a therapeutic device for supplying beneficial light to organic tissue including a carrier (in the form of a human mask) containing an array of single frequency LED's. The power supply provides a fluctuating or pulsating output voltage.

U.S. Pat. No. 4,646,743 to Parris discloses therapy radiation apparatus for veterinary medicine which include arrays of infrared LED's. The LED arrays can be mounted in flexible means for wrapping about the outer surfaces of an animal, or in the form of rigid probes for irradiating internal surfaces. Devices referring to this patent are produced commercially under the BIOSCAN™ trademark.

U.S. Pat. No. 5,660,461 to Quantum Devices, Inc. discloses LED arrays assembled from pluralities of modular units which are snapped together. Reflector units are provided to direct the radiation. The modules can be electrically connected together in series or parallel. The arrays can be used to stimulate plant growth or for photo-dynamic therapy.

U.S. Pat. No. 5,445,608 discusses various methods of photo-dynamic therapy, and discloses methods and apparatus for providing such therapy by employing an implantable probe to illuminate internal treatment sites which have been perfused with photo-reactive agents. The apparatus can include arrays of LED's or solid-state laser diodes.

Review of a selected portion of the patents discussed above documents that photo-therapy has become an accepted and established modality for the noninvasive and safe treatment of

- burns, cuts and abrasions,
- muscle, tissue and tendon repair,
- cancerous tumors,
- herpes,
- arthritis and other inflammations,
- the stimulation or sedation of acupressure meridian points in humans and animals,
- bone fracture repair, and
- stimulation of plant growth.

SUMMARY OF THE INVENTION

It is a primary object of the present invention to improve upon the prior art devices and expand the usefulness of the methodology of photo/light therapy.

The present invention is an improvement of recent patented photo-therapy devices as well as photo-therapy devices we have been testing for approximately three years. Preferred embodiments of present day photo-therapy devices have certain limitations. Firstly, they are designed to be used "on or near the skin surface" in order to be effective. This is a drawback in many scenarios—such as in large ranching operations where it is typical for livestock (cow, bull, horse) to injure itself on the range—perhaps a few miles to hundreds of miles from the nearest clinic. An animal of 1000–3000 pounds in pain and duress needs to be considered dangerous and puts the practitioner at considerable risk. The present invention allows for the therapeutic treatment to take place at a distance of approximately ½ foot to several feet away, thus assuring the safety of the practitioner while bringing pain relief and healing to the animal being treated.

Also in the case of severe burns where infection is an acute problem and rapid skin rejuvenation can make the difference between life and death, the present invention can effectively be used at a more comfortable distance from the patient's skin surface without excessive pain from close contact of "on or near the skin surface" of other prior art photo-therapy devices. There is documentation that treatment with photo-therapy increases the healing process to take place much faster than without photo-therapy being applied, and therefore raises skin resistance to infection and other septic/toxic poisoning. (Hospitals refer to slow healing as "dysfunctional healing" because it allows for depressed immune systems, surgical complications, joint contracture, scar tissue growth, and even depression to set in before significant healing can begin).

Another advantage of having the capability or option of working from a distance is that the LED's (unlike lasers) diffuse as the unit gets further and further away from the object being illuminated. Thus a larger area—double, triple or more—can effectively be covered. This allows for a manufacturing savings because an LED unit having a 6 inch radius, when positioned on or near a surface, can only illuminate about 6–8 inches. However, the same 6 inch radius LED unit, working from a distance of several feet, can illuminate an area of 12 inches, 24 inches, 40 inches, etc., depending on the amount of power (energy level in watts), high intensity of the LED's, and the time treatment duration. (Increased duration or time of treatment needs to be adjusted, the further from the surface).

Another advantage of the present invention is the ability of the user to program or compose his/her own settings—which may effectively need to vary from one individual to another, instead of being limited to the pre-determined settings of other prior art devices. A separate computer might be connected to the light-emitting device for this purpose.

Yet another advantage is the "flicker fusion phenomenon", a theta wave setting at about 3–5 hertz which causes brain neurotransmitters (chemicals and electromagnetic charges) to be produced and fired off to give a relaxation effect, a drop in heart rate, drooping eyelids, etc. Many tests which were carried out in the 1950's, especially in mental institutes, indicated that the "relaxation effect" was an important ingredient in the overall health and mental stability of the patient. More recent tests conclude that relaxation (also accomplished through guided visualizations, music of nature sounds such as running water and birds chirping, hypnosis and meditation techniques) enhance traditional healing modalities (drug therapy and surgery) especially in cases of heart attack and terminal illnesses and such relaxation practices are presently being offered in some major hospitals such as Columbia Presbyterian in New York City.

Another advantage of this invention is that one program setting is the "Wave Effect Frequency"—alternating colors rippling in succession from head to foot, again and again. (i.e., IR, then red, then orange, then green, then blue in slow succession, rapid succession or slow to rapid succession). This unit might be embodied in something resembling a tanning bed.

Another improvement is the pre-set program to control a decrease or increase in power outage. Some requirements might call for "soft" energy (low wattage amount delivered over a longer time duration) while others call for a "bursting" effect (high wattage delivery for short durations).

Yet another advantage is that the use of high intensity IR diodes inexpensively adds a hypothermia effect without the additional cost of heat sinks, resistors, etc. (which add expense to the manufacturing process).

The present invention's ability to choose only one wave frequency (color) at a time gives an added advantage. It is well accepted in therapeutic injury repair that the first 24–48 hours after an injury ice or cold compresses should be used, then heat or warmth such as an IR heat lamp, heating pad, or muscular creams such as Ben-gay or tiger balm.

The present invention can allow one device for both cold and heat treatments, with the added advantage of the red-wave frequency for immediate pain relief and/or bleeding reduction, decrease in inflammation and increase in energy flow, and a predisposition to inhibit infection. In this scenario, first the red-wave frequency would be used until desired results were obtained. Thereafter, the blue wave frequency (cools, soothes, reduces irritability of skin surface) would be applied. Lastly, the IR wave frequency, which causes a thermal effect, would be applied.

In case of illness or emotional trauma or stress these three wave frequencies would be more effective if used simultaneously rather than consecutively as explained above.

The present invention does not preclude the addition of other modalities or art forms to be used in combination with this preferred embodiment, as research data becomes available for increased effectiveness of adding such forms. These include, but are not limited to, magnets and magnetic therapy; audio sounds, ultra-sound and audio waves; electroplated holograms/holoforms; electromagnetic devices; and words or symbols having a significant intent.

Another advantage over prior art devices is in the methodology of "Whole Body Treatment". The construction of larger units than now available and/or the capability of working at a distance away from the skin surface allows for the timely and advantageous treatment of the entire body structure rather than the limited treatment of a localized area or spot. Thus, three body systems are being covered in one usage, saving time and money. These three systems are the physical/skeletal, the acupuncture meridian, and the bio-electromagnetic energy field. (This later system has thus far been less traditionally researched by the Western World, but the encyclopedia-size book by Dr. Richard Gerber, M.D. Vibrational Medicine (Bear and Co., Santa Fe, N.Mex. 1988), substantiates and clinically documents the existence and importance of this "E-Field").

Other objects and advantages of this invention will become apparent from perusal of the following detailed description, drawings and the appended claims, the drawings forming a part of the specification wherein like reference numerals designate corresponding parts in the several views.

Before explaining the disclosed embodiments of the present invention in detail, it is to be understood that the invention is not limited in its application to the details for the particular arrangements shown, since the invention is capable of other embodiments. Also, terminology used herein is for the purpose of description, not of limitation.

DESCRIPTION OF THE PREFERRED EMBODIMENTS

Figure 1:
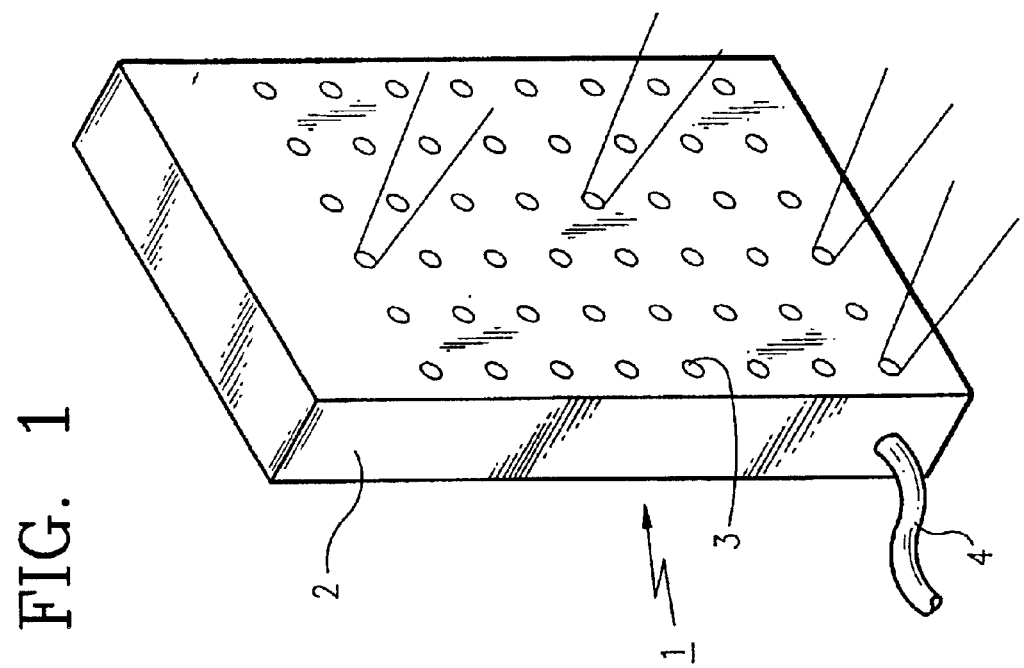
FIG. 1 is a perspective view of a light panel for a photo-therapy device in accordance with a first embodiment of the invention.
Figures 1A, 3A:
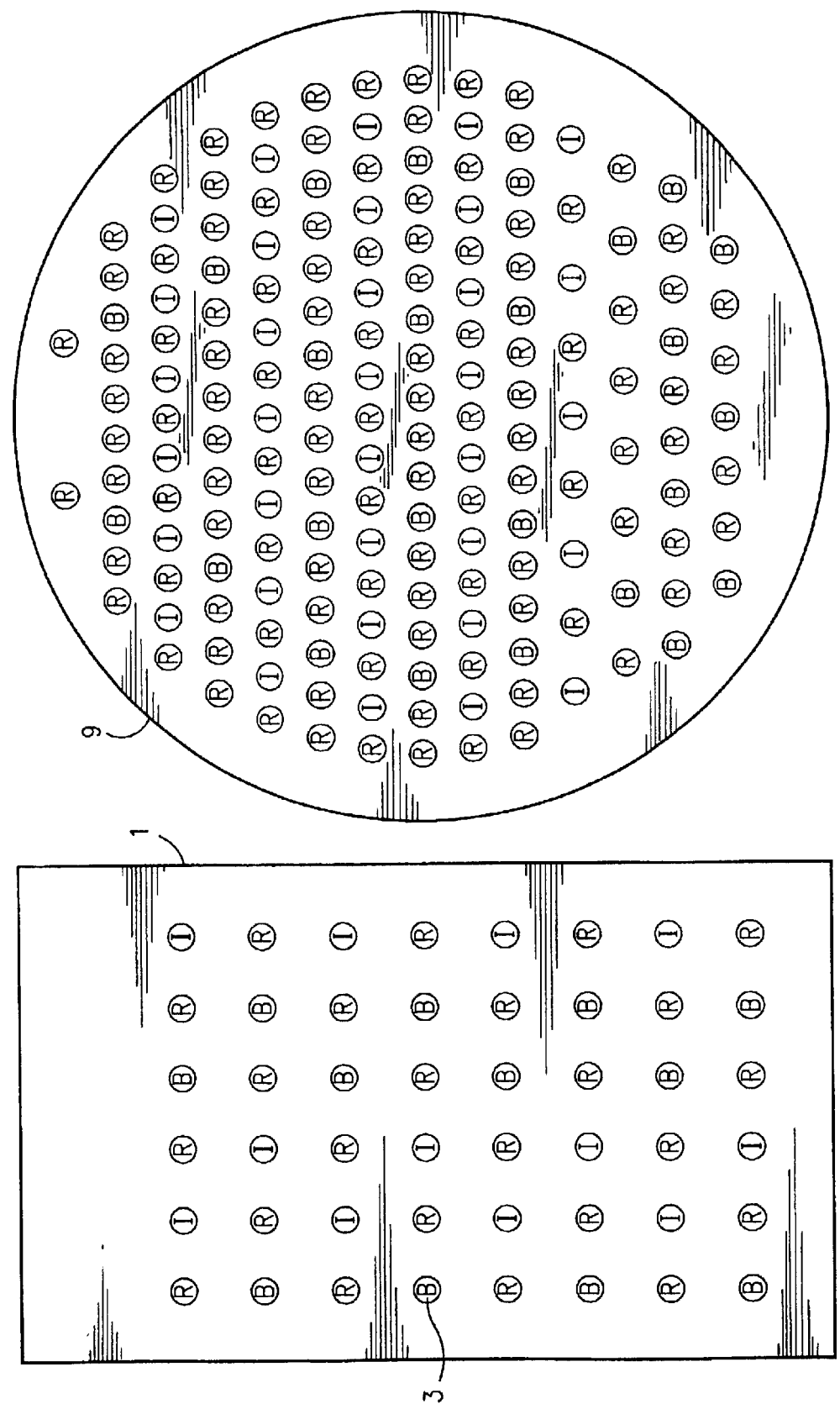
FIG. 1A shows schematically the arrangement and color output of the light sources for the light panel of FIG. 1.
FIG. 3A shows schematically the arrangement and color output of the light sources for the light panel of FIG. 3.

All of the preferred embodiments explained below can be used for animals, humans, plants or for any living organism Referring now to FIG. 1, there is shown one embodiment of the present invention which is of general use for living organisms. The LED unit 1 has a generally box shaped housing 2 with a plurality of LED's 3 arranged in an array of rows and columns. There is an electrical connection 4 near the bottom of the housing 2 leading to a control box 5 which will be explained later. The approximate dimensions of LED unit 1 are 7.4×4.7×1.3 inches (these dimensions are not critical and may vary). The physical spatial arrangement of the LED's are shown in FIG. 1A where the red emitting LED's are designated by R in the circles, the IR emitting LED's are designated by I in the circles and the blue emitting LED's are designated by B in the circles. There are 48 LED's in all, 24 LED's emitting red light at 630 nm, 12 LED's emitting infrared (IR) light at 880 nm, and 12 LED's emitting blue light at 470 nm. The LED array has 6 columns of LED's and 8 rows of LED's. In the first column of the LED array, starting with a red emitting LED, the red emitting LED appears at every other one with a blue emitting LED inbetween; thus, there are four red emitting LED's and four blue emitting LED's. In the second column of the LED array, starting with an IR LED, there appears an IR LED at every other one with a red emitting LED inbetween; thus, there are four IR LED's and four red emitting LED's. In the third column of the LED array, starting with a red emitting LED, there appears a red emitting LED at every other one with an IR LED inbetween; thus, there are four red emitting LED's and four IR LED's. In the fourth column of the LED array, starting with a blue emitting LED, there appears a blue emitting LED at every other one with a red emitting LED inbetween; thus, there are four blue emitting LED's and four red emitting LED's. The fifth column arrangement of LED's is similar to the first column arrangement of LED's and the sixth or last column arrangement of LED's is similar to the second column arrangement of LED's. The number of LED's in the array and, consequently, the size of the housing 2 may vary depending on the particular application. The red, blue and IR light emitting LED's, as well as their availability, are well known in the art and, therefore, are not explained further.

Figure 2:
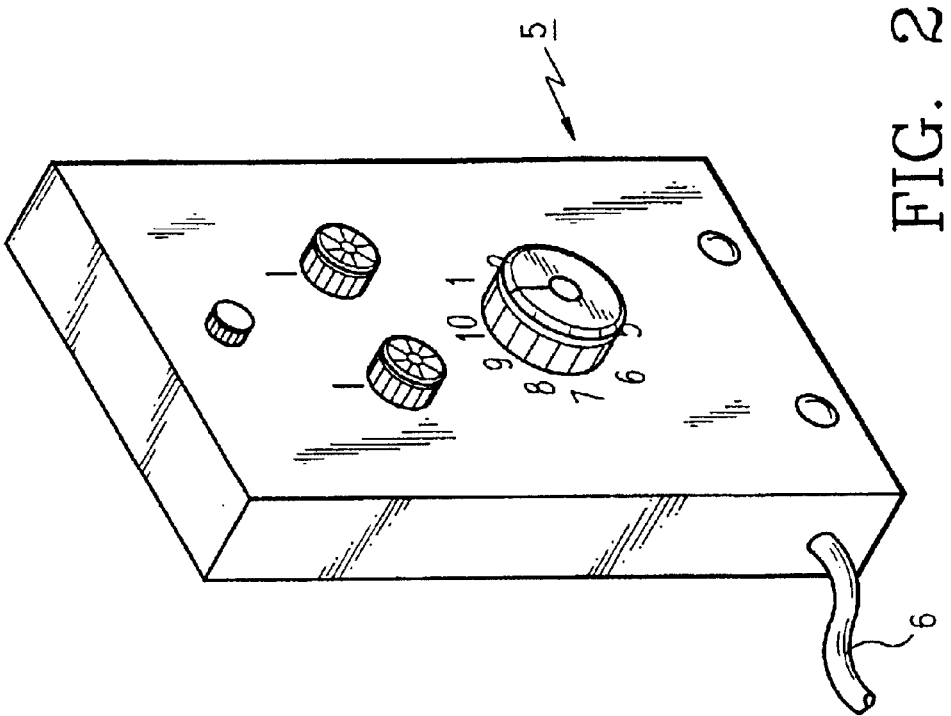
FIG. 2 is a perspective view of a control panel for the light panel of FIG. 1.

Referring now to FIG. 2, there is shown a control box 5 which is electrically connected to LED unit 1 (shown in FIG. 1) via an electrical connection 6. The control box 4 contains circuitry therein and has several control knobs for controlling various aspects of the LED array. The circuitry and functions of the control knobs will be explained later.

Figure 3:
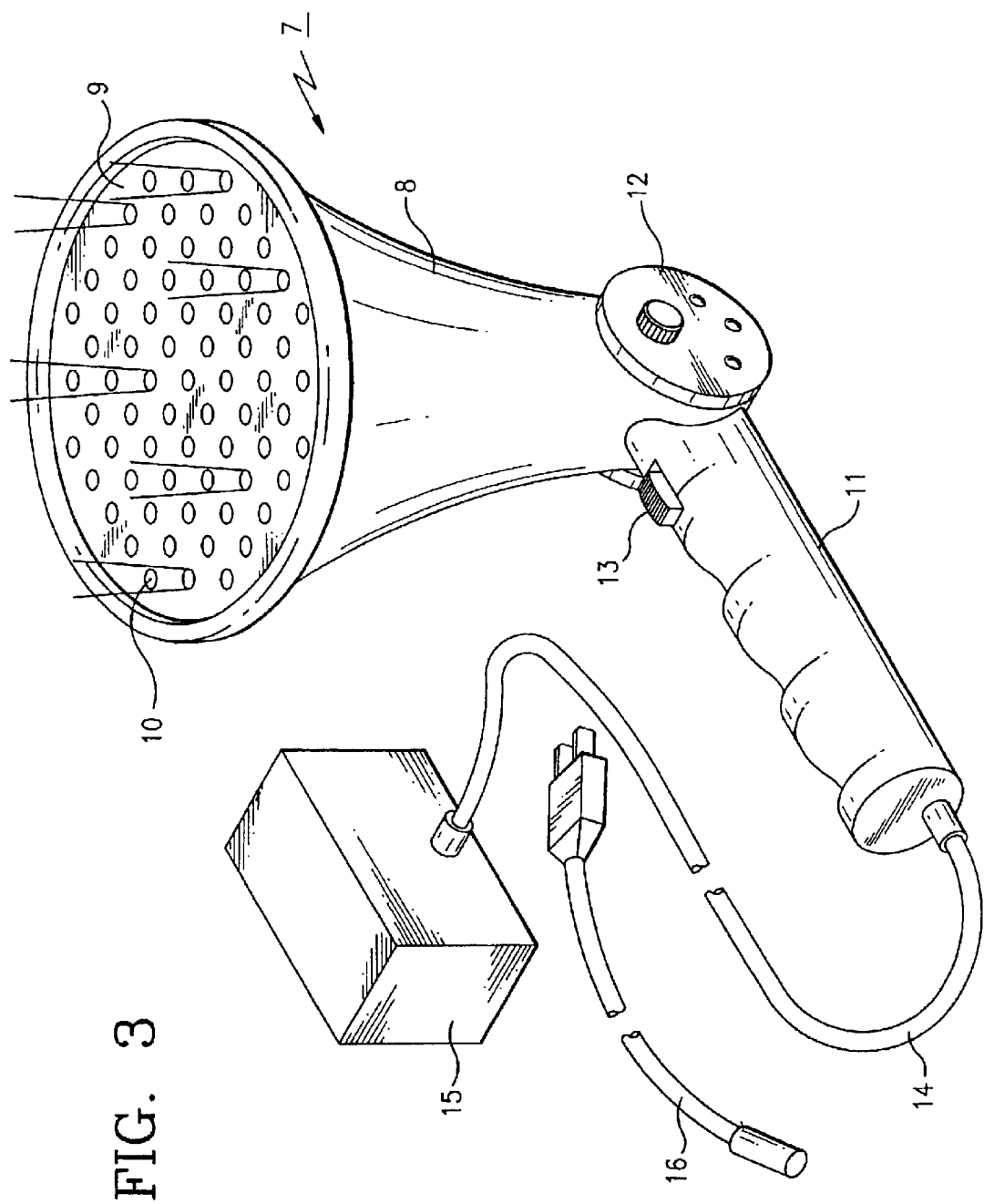
FIG. 3 is a perspective view of a hand-held model of a photo-therapy device in accordance with a second embodiment of the invention.

FIG. 3 shows a portable, hand held model 7 of the present invention. The hand held model 7 has a frusto-conical shaped housing 8 with a disk shaped support 9 for a plurality of LED's 10 arranged in a patterned array. Attached to the housing 8 is a handle 11 and a control knob 12. The handle 11 has an on/off switch 13 and an electrical connection 14 which is connected to a control box 15. This hand held model 7 is also provided with an electrical ac plug-in connector 16 for the control box 15. The LED support 9 contains 184 LED's arranged in a particular pattern. The patterned array contains 119 red emitting LED's, 40 IR emitting LED's and 25 blue emitting LED's. The particular physical spatial arrangement of LED's is shown in FIG. 3A where the red emitting LED's are designated by R in the circles, the blue emitting LED's are designated by B in the circles and the IR emitting LED's are designated by I in the circles. The support disk 9 has a diameter of approximately 8 inches and the length of the handle 11 is approximately 5 and ⅞ inches (these dimensions are not critical and may vary).

Figure 4:
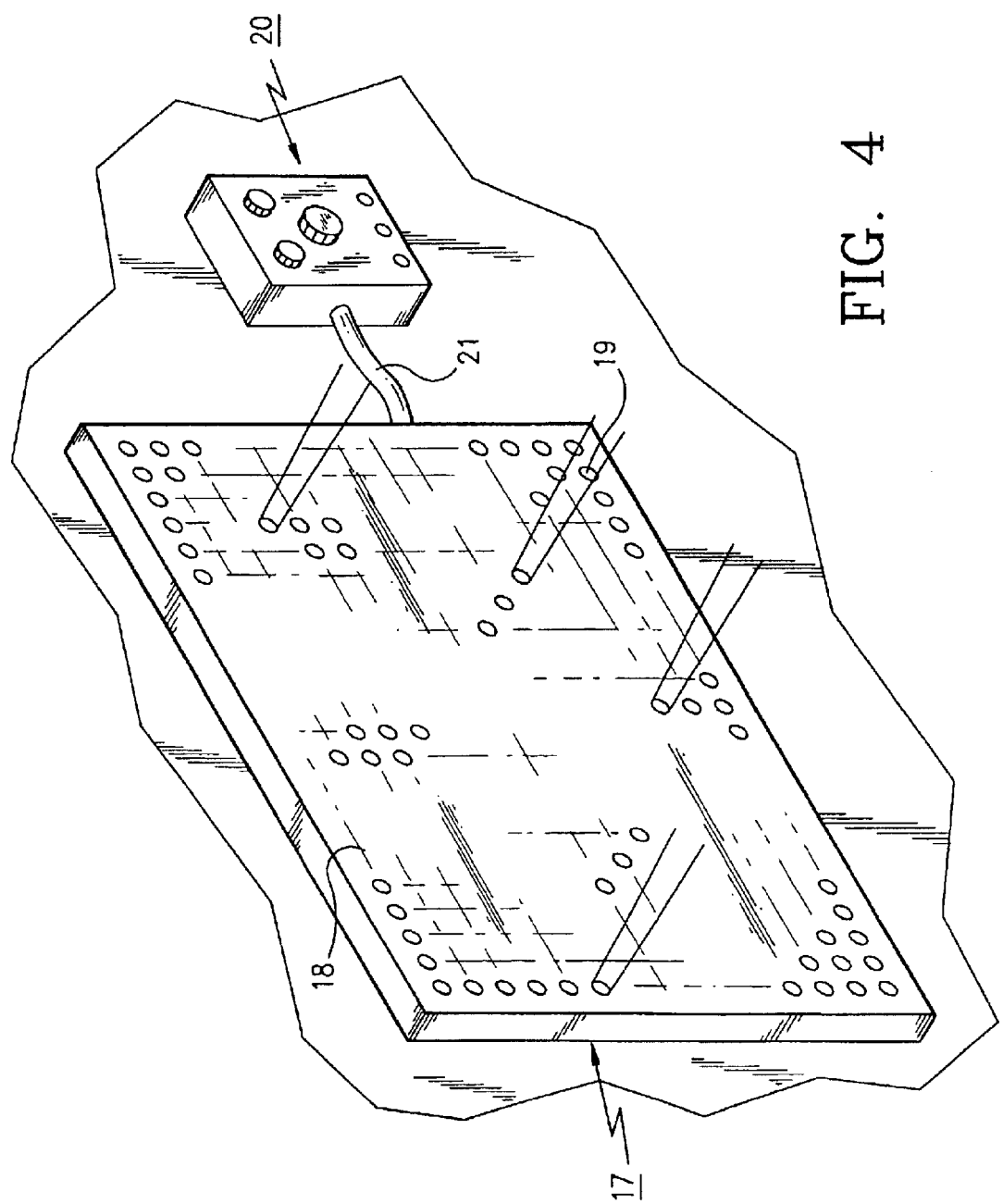
FIG. 4 is a perspective view of a large, wall-mounted photo-therapy device according to a third embodiment of the invention.

FIG. 4 shows yet a further embodiment of the present invention. A photo-therapy device 17 takes the form of a wall panel 18. The wall panel 18 has dimensions of 3 feet by 6 feet by 3 inches; however, the size of the wall panel 18 may vary depending on the size of the subject or object being treated. The wall panel 18 has 24 LED's 19 in each column along its smaller dimension of 3 feet and 48 LED's in each row along its larger dimension of 6 feet. There are a total of 1,152 LED's in the wall panel 18; 230 LED's emitting red light at 630 nm, 230 LED's emitting IR light at 880 nm, 231 LED's emitting blue light at 470 nm, 231 LED's emitting green light at 565 nm and 230 LED's emitting amber light at 590 nm. Each LED emitting in a particular color (wavelength) would alternate in a repeated pattern, for example, blue, green, amber, red, IR (repeat, etc.). The LED's 19 in the wall panel 18 are connected to the control box 20 with its control knobs. The wall panel 18 if attached to a wall at an appropriate height and a person, animal or plant would be positioned in front of it for treatment. The subject of the photo-therapy treatment is positioned in front of the wall panel 18 for an appropriate amount of time at a distance from close proximity to several feet. For example, a wall panel 18 is hung on each side of a horse trailer (inside) and a horse placed between the wall panels 18 for treatment. Another example, a bull rider or horseback rider who is in need of treatment stands between the wall panels 18 in the horse trailer or in a similar enclosure at a competitive event and is treated for relaxation, pain relief or healing. Plants could also be placed in a room with a wall panel 18 on each side of the room and be treated by the light generating from the LED's of the wall panels in order to obtain faster and stronger plant growth.

Figure 5:
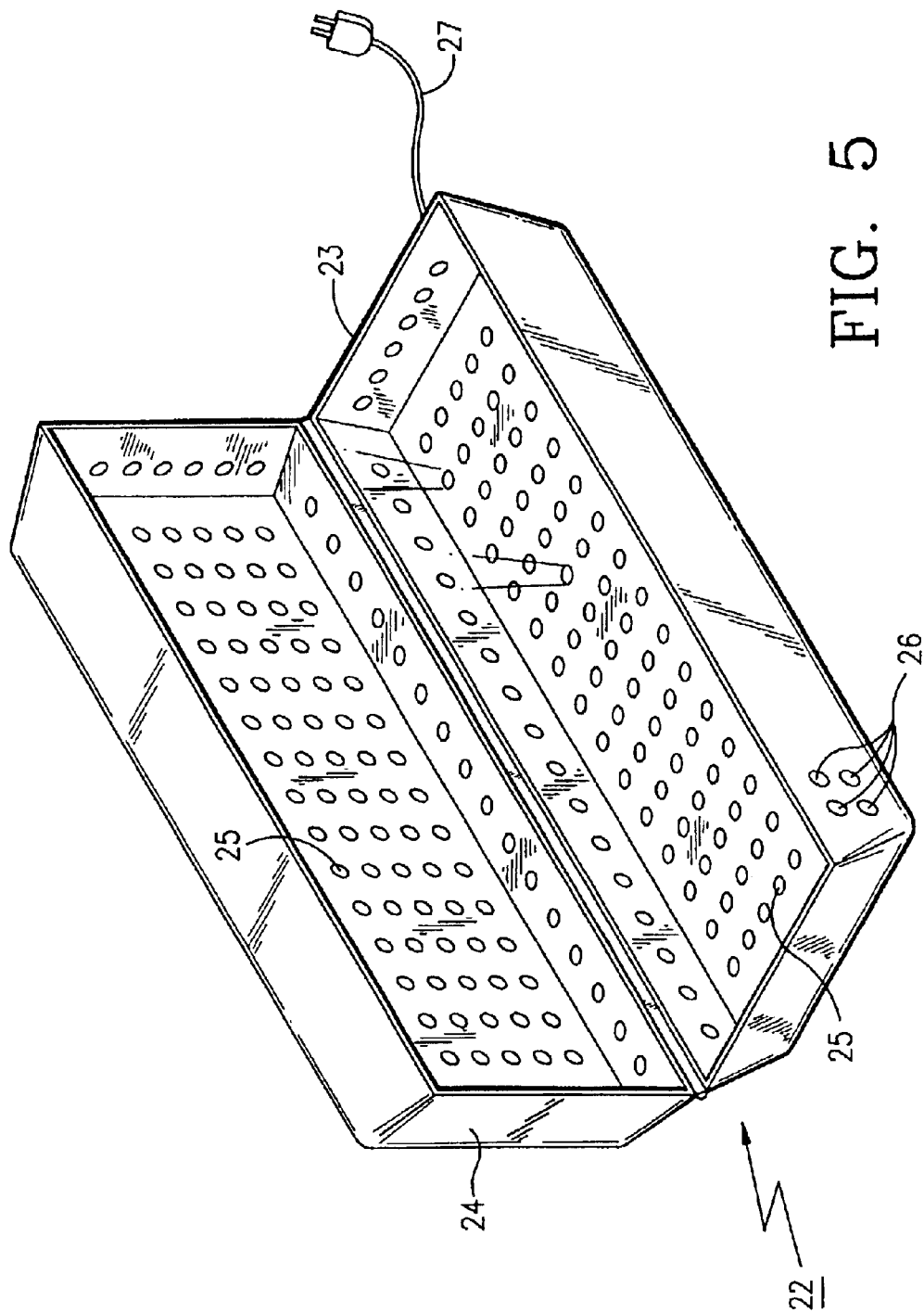
FIG. 5 is a perspective view of a photo-therapy device according to a fourth embodiment of the invention wherein the device is configured as a receptacle resembling a tanning bed with the lid open.
Figure 5A:
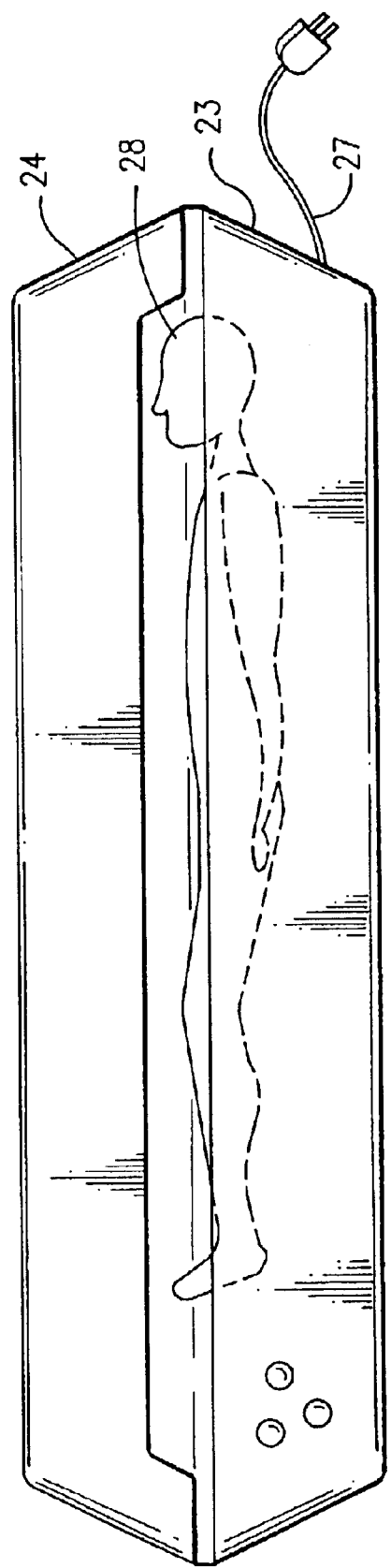
FIG. 5A is a perspective view of the photo-therapy device of FIG. 5 with a patient in the receptacle and the lid partially closed.

Referring now to FIG. 5, there is shown another embodiment of a photo-therapy device of the present invention which is used primarily for humans. The photo-therapy device takes the form of a full body bed 22 with a hollow enclosure 23 and a lid 24 and LED's embedded within the hollow enclosure 23 and lid 24. The full body bed 22 has the following dimensions: 3 feet wide, 6 ½ feet long and a 20 inch depth; obviously, these dimensions could vary. A control box (not shown) is built into the front side of the hollow enclosure 23 and control knobs 26 are connected to the control box. An electrical cord 27 will connect the control box to an electrical outlet or generator. There are a total of 2,304 LED's inside the full body bed 22 with 1,152 LED's on the inside of the lid 24 and 1,152 LED's on the inside floor of the hollow enclosure 23. On the inside of the lid 24, there are 230 LED's emitting red light at 630 nm, 230 LED's emitting IR light at 880 nm, 231 LED's emitting blue light at 470 nm, 565 LED's emitting green light at 565 nm and 230 LED's emitting amber light at 590 nm. The numbers of specific LED's emitting in a particular wavelength on the inside of the hollow enclosure 23 are the same as those on the inside of the lid 24. Each LED for a given wavelength alternates in a repeated pattern, for example, blue, green, amber, red and IR. A person for treatment would lie down in the full body bed 22, face up, with the lid 24 partially closed; the photo-therapy treatment would provide a relaxation effect, pain reduction or healing of the person. This embodiment of the invention could also be used in a hospital or nursing home for the treatment of bedsores or it can be combined with piped-in music and thus produce a "wave effect" for deep relaxation or pain relief alter an operation. It could also be used to stimulate the immune system of a human with a disease such as cancer, etc. FIG. 5 shows the full body bed 22 with the lid 24 in the fully open position whereas FIG. 5A shows a patient 28 lying within the full body bed 22 for treatment with the lid 24 being partially closed.

Figure 6A:
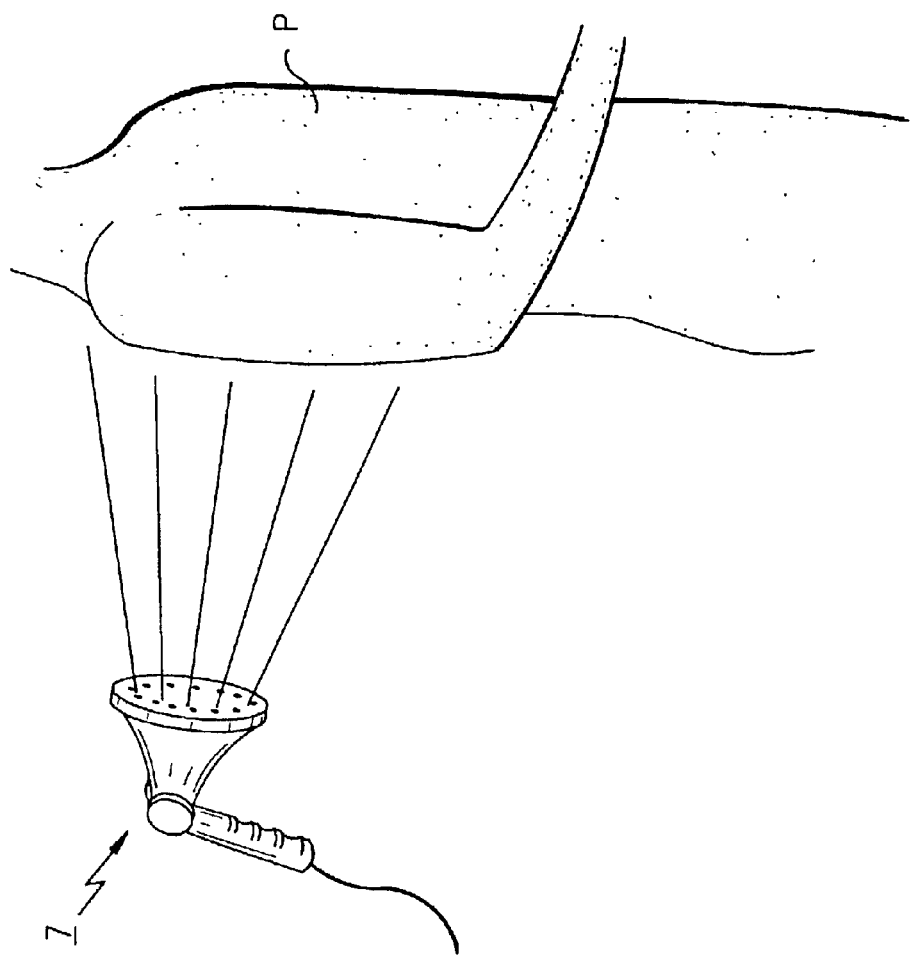
FIG. 6A shows the hand-held model of FIG. 3 in operation at a remote distance from a patient being treated.
Figure 6:
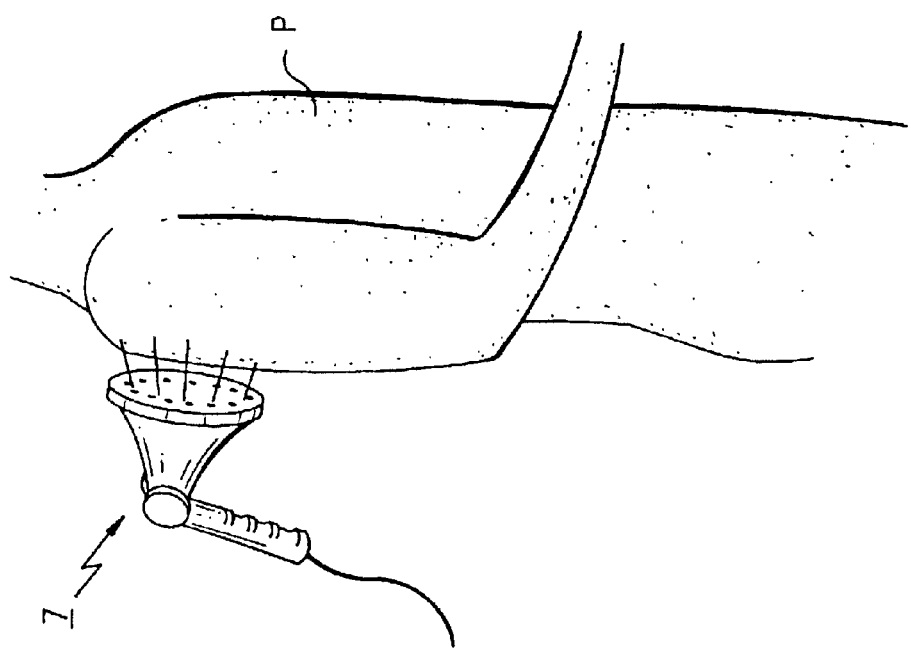
FIG. 6 shows the hand-held model of FIG. 3 in operation in close proximity to a patient being treated.

FIG. 6 shows an application of the hand held model 7 of the present photo-therapy device being applied in close proximity to a small body area of a patient P being treated whereas FIG. 6B shows the photo-therapy device being applied to a larger body area of a patient P being treated, the latter application demonstrating a diffusion effect of the device.

Figure 7:
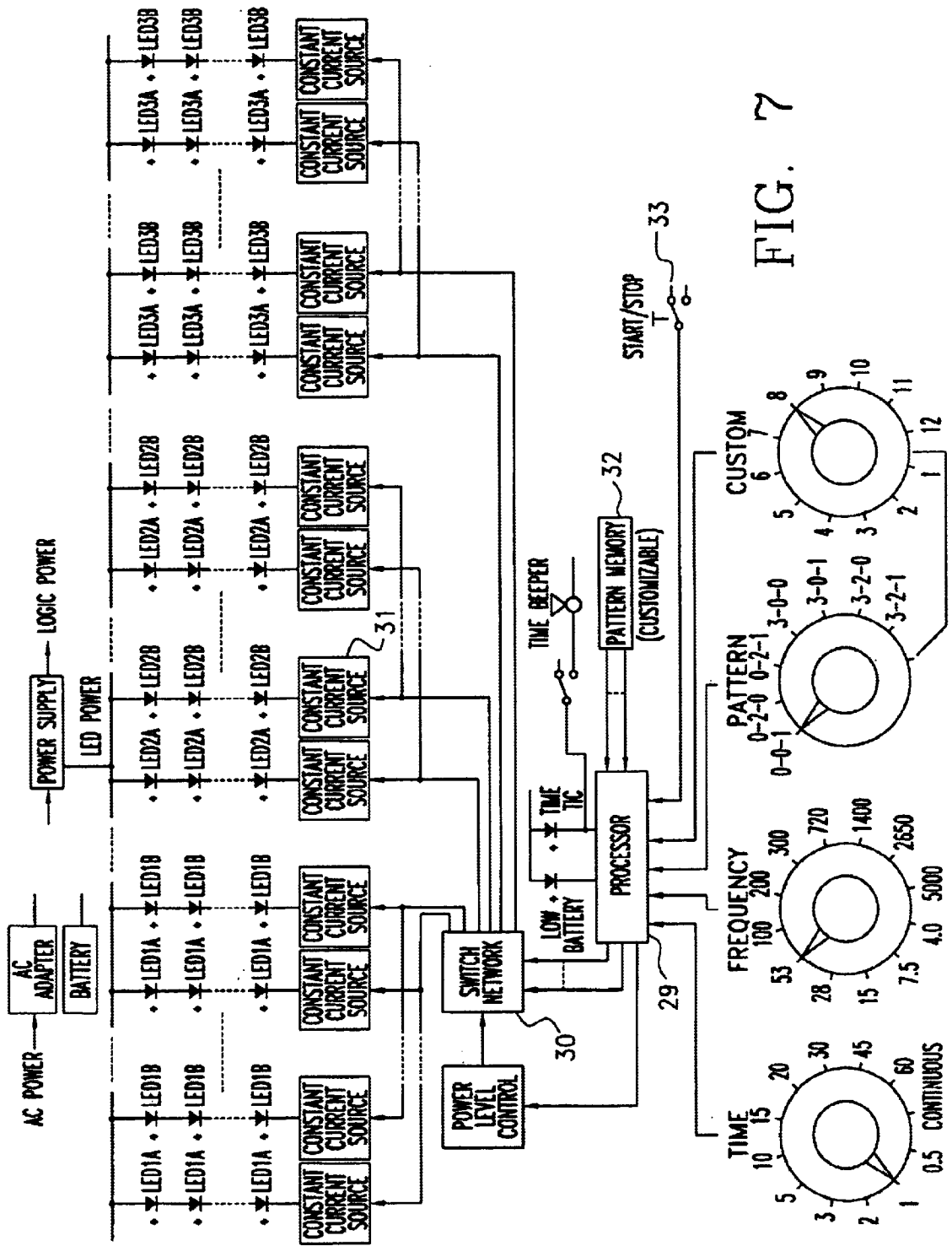
FIG. 7 is a schematic of the circuit for operating the photo-therapy devices of this invention.
Figure 7A:
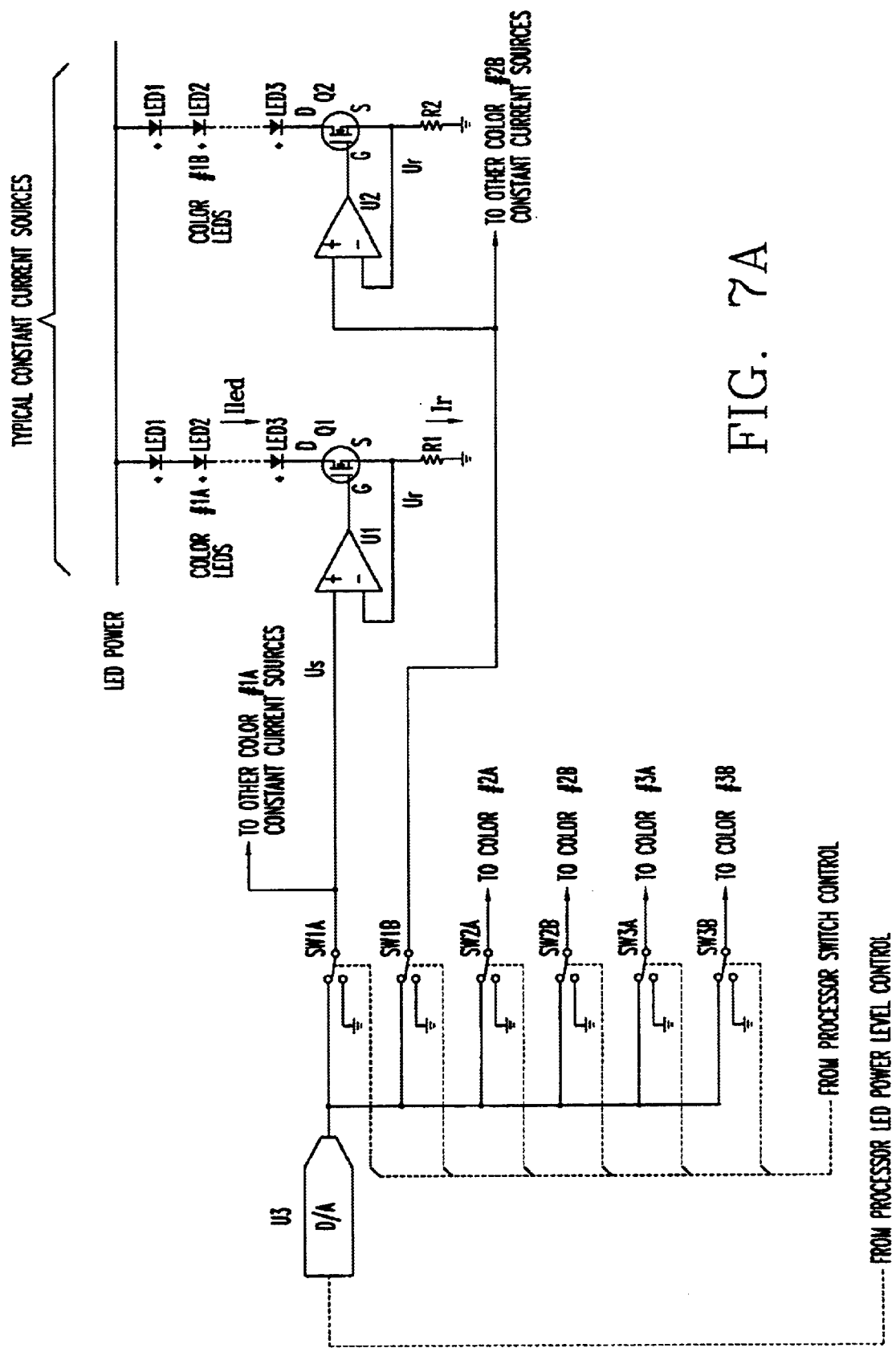
FIG. 7A is a circuit diagram of the SWITCH NETWORK and CONSTANT CURRENT SOURCE of the operating circuit shown in FIG. 7.

FIGS. 7 and 7A are circuit diagrams showing how the LED's of the various embodiments of this invention are connected to a control box with control knobs for controlling or regulating the operation of the LED arrays in the various embodiments. The circuit diagrams show the general scheme of a photo-therapy device of this invention that is designed to provide a luminous pattern for a specific therapeutic application. The geometric pattern and color(s) of the LED array, the frequency and duty cycle of the LED array and the total time of operation of the photo-therapy device can be varied to satisfy the requirements of an intended therapeutic application.

For example, FIG. 7 shows a circuit diagram for a photo-therapy device of the present invention which operates three different light source types (LED 1, LED 2 and LED 3) each of which is energized independently by a processor 29 (or microprocessor) via a switch network 30. The series strings of a particular light source type (LED 1, LED 2 and LED 3) are divided into two groups, A and B, as shown in the circuit diagram. Each group A and B of series light strings will normally be switched on and off in an alternate fashion to minimize the maximum power requirements of the system. Each series of light strings A and B is energized by a constant current source 31 that insures proper operation of the photo-therapy device under varying conditions of temperature and supply voltage. In some therapeutic applications, the value of the constant current can be modified under the control of the processor 29 to conform to a custom pattern. The processor operation is controlled by the operator of the photo-therapy device by the setting of the control switch positions for TIME, FREQUENCY, PATTERN and CUSTOM. The TIME control switch will set the desired period of operation, the FREQUENCY control switch will set the alternating on/off rate between the A and B groups of light strings, the PATTERN control switch will directly select which light source type(s) (LED 1, LED 2 or LED 3) to be energized or will select the CUSTOM mode of operation, and the CUSTOM control switch will select which pattern from the pattern memory module 32 that the processor 29 is to perform In this mode, the processor 29 can vary the time, frequency, power level and light source strings in any prearranged (programmed) sequence. For example, the processor 29 can be preprogrammed to provide the following patterns of illumination: a) each color set on individually, b) all color sets on simultaneously, c) at least two color sets on simultaneously and d) at least two color sets on for preset periods of time. The processor 29 may also be programmed to sequentially pulse the LED sets of the photo-therapy device to emit light of different colors. The control circuit may also be adjusted for pulsed operation of at least two sets of LED's with pulse durations of in the range of from about 0.001 sec. to about 0.2 sec. and pulse repetition rates in the range of from about 4 Hz to about 10,000 Hz. The pulse duration may be approximately half the period of each cycle. The processor 29 can also provide indications of low battery level and an elapsed time of operation in the form of a lamp and, if enabled, an audible beep. For an indication of the elapsed time of operation, the treatment timer may be connected to a visual or audio means for indicating the remaining treatment time. Although the means for indicating low battery level and elapsed time of operation are not shown, the addition of such means to the circuitry and equipment of the present invention would be obvious to one skilled in the art and is, therefore, not detailed here.

The operation of each of the photo-therapy devices disclosed herein is started by depressing the START/STOP push button 33 shown schematically in FIG. 7 and a second depression of the pushbutton 33 will stop the operation independently of the time setting.

Typical applications of the photo-therapy devices described above do not preclude the use of keyboards for operator input, alternate displays for status information or the use of an external computer for control of the operation of the devices.

The block diagram of FIG. 7 shows the use of Light Emitting Diodes (LED's) which operate over the application-specific spectrum. However, the general scheme is not limited to LED's but other light sources may be used such as incandescent lamps. The light sources are shown in a series connection to improve electrical efficiency. Light sources of the same or different colors may be grouped as required for a particular application,. Light sources for the photo-therapy devices of this invention may include both the visible and invisible portions of the frequency spectrum. Although FIG. 7 shows that all the light sources in a given group are enabled at the same time, individual control of series strings is not precluded.

The block diagram shown in FIG. 7A shows the light sources being driven by constant current sources on the low voltage side of the power supply. However, control from the high voltage side of the power supply is not precluded. A typical constant current source operating on the low voltage side of the power supply is shown in the block diagram of FIG. 7A and consists of an operational amplifier U1, an FET transistor Q1 and a resistor R1. U1 will cause Q1 to conduct enough current Ir to satisfy the relationship Vs=Vr=Ir×R1 or Iled=Ir=Vs/R1. Thus, the current through the LED's, i.e., Iled, is a function of Vs and R1 and independent of the varying characteristics of the LED's as a function of temperature, power levels and individual parts. The value of Vs is determined by the switch position (SW1A, SW1B, etc.) and is either the output of the digital-to-analog converter D/A or 0 volts. Since both the switch and the converter D/A are under control of the processor 29, the individual light source strings can be turned on and off at various power levels as required by the program.

The power supply for the block diagram circuit of FIG. 7 is normally a direct current (DC) voltage source converted from the normal house supply or a battery. Alternative well known power sources can also be used. The power to drive the photo-therapy devices of this invention ranges from 10 W/cm2 to 30 W/cm2.

Modifications of this invention will be readily apparent to those skilled in the art and it is intended that the invention be not limited by the embodiments disclosed herein but that the scope of the invention be defined by the appended claims.

What is claimed is:

1. A photo-therapy device comprising an enclosure having a hollow shaped bottom and a movable lid attached to said bottom, an array of LED's arranged in a predetermined pattern in said lid, an array of LED's arranged in a predetermined pattern in said bottom, said arrays of LED's emitting visible and high intensity infrared light, a control circuit housed within said hollow shaped bottom or in said lid, said control circuit being electrically connected to said arrays of LED's for controlling the operation of said arrays of LED's, control knobs being attached externally to said hollow shaped bottom or said lid and said control knobs being electrically connected to said control circuit.

2. The photo-therapy device of claim 1 wherein said array of LED's in said bottom has the same number of LED's in said lid.

3. The photo-therapy device of claim 2 wherein each said array of LED's being arranged in the same predetermined pattern.

4. The photo-therapy device of claim 3 wherein said LED's in each array emitting light in five different wavelengths.

5. The photo-therapy device of claim 4 wherein said five different wavelengths are 470 nm, 565 nm, 590 nm, 630 nm and 880 nm.

6. The photo-therapy device of claim 1 wherein the majority of LED's in said lid array face directly towards said bottom.

7. The photo-therapy device of claim 6 wherein the majority of LED's in said bottom array face directly towards said lid.

8. The photo-therapy device of claim 1 wherein the majority of LED's in said bottom array face directly towards said lid.

9. A photo-therapy device comprising an enclosure having a hollow shaped bottom and a movable lid attached to said bottom, an array of LED's arranged in a predetermined pattern in said lid, an array of LED's arranged in a predetermined pattern in said bottom, said array of LED's in said bottom has the same number of LED's in said lid, each said array of LED's being arranged in the same predetermined pattern, said LED's in each array emitting light in five different wavelengths, a control circuit housed within said hollow shaped bottom or said lid, said control circuit being electrically connected to said arrays of LED's for controlling the operation of said arrays of LED's, control knobs being attached externally to said hollow shaped bottom or said lid and said control knobs being electrically connected to said control circuit.

10. A photo-therapy device comprising an enclosure having a hollow shaped bottom and a movable lid attached to said bottom, an array of LED's arranged in a predetermined pattern in said lid, an array of LED's arranged in a predetermined pattern in said bottom, said array of LED's in said bottom has the same number of LED's in said lid, each said array of LED's being arranged in the same predetermined pattern, said LED's in each array emitting light in five different wavelengths wherein said five different wavelengths are 470 nm, 565 nm, 590 nm, 630 nm and 880 nm, a control circuit housed within said hollow shaped bottom or said lid, said control circuit being electrically connected to said arrays of LED's for controlling the operation of said arrays of LED's, control knobs being attached externally to said hollow shaped bottom or said lid and said control knobs being electrically connected to said control circuit.

* * * * *